United States Patent
Zilch et al.

[11] Patent Number: 6,136,797
[45] Date of Patent: *Oct. 24, 2000

[54] PHOSPHOLIPID DERIVATIVES OF PHOSPHONO-CARBOXYLIC ACIDS, THE PRODUCTION OF SAID DERIVATIVES AND THE USE OF SAID DERIVATIVES AS ANTIVIRAL MEDICAMENTS

[76] Inventors: Harald Zilch, Alsenweg 24, D-68305 Mannheim; Dieter Herrmann, Bothestrasse 54/1, D-69126 Heidelberg; Hans-George Opitz, Im Netztal 46, D-69469 Weinheim; Gerd Zimmermann, Dornheimer Ring 4, D-68309 Mannheim, all of Germany

[*] Notice: This patent issued on a continued prosecution application filed under 37 CFR 1.53(d), and is subject to the twenty year patent term provisions of 35 U.S.C. 154(a)(2).

[21] Appl. No.: 09/077,891
[22] PCT Filed: Dec. 16, 1996
[86] PCT No.: PCT/EP96/05647
  § 371 Date: Aug. 27, 1998
  § 102(e) Date: Aug. 27, 1998
[87] PCT Pub. No.: WO97/22613
  PCT Pub. Date: Jun. 26, 1997

[30] Foreign Application Priority Data
Dec. 15, 1995 [DE] Germany .................. 195 47 023
Oct. 22, 1996 [DE] Germany .................. 196 43 416

[51] Int. Cl.[7] .............. A61K 31/66; C07F 9/40; A61P 31/12
[52] U.S. Cl. .......... 514/120; 514/114; 514/119; 558/169; 558/172; 558/174; 558/179; 558/181
[58] Field of Search .................. 558/179, 181; 514/120

[56] References Cited

U.S. PATENT DOCUMENTS

| | | | |
|---|---|---|---|
| 5,194,654 | 3/1993 | Hostetler et al. | 558/181 X |
| 5,696,277 | 12/1997 | Hostetler et al. | 554/49 |

*Primary Examiner*—Michael G. Ambrose
*Attorney, Agent, or Firm*—Arent Fox Kintner Plotkin Kohn

[57] ABSTRACT

The present invention concerns new lipid derivatives of phosphonocarboxylic acids of the general formula I,

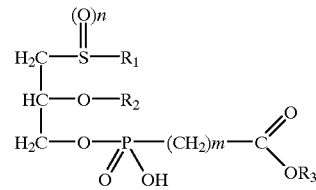

in which the meaning of the symbols is elucidated in the description, tautomers thereof and their physiologically tolerated esters and salts of inorganic or organic bases as well as processes for the production thereof and pharmaceutical agents containing these compounds.

8 Claims, No Drawings

PHOSPHOLIPID DERIVATIVES OF PHOSPHONO-CARBOXYLIC ACIDS, THE PRODUCTION OF SAID DERIVATIVES AND THE USE OF SAID DERIVATIVES AS ANTIVIRAL MEDICAMENTS

The present invention concerns new lipid derivatives of phosphonocarboxylic acids and their esters of the general formula I,

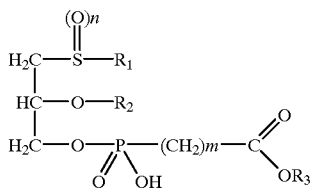

in which
R$^1$ is a straight-chained or branched, saturated or unsaturated alkyl chain with 9–13 carbon atoms,
R$^2$ can be a straight-chained or branched, saturated or unsaturated alkyl chain with 8–12 carbon atoms
R$^3$ represents hydrogen, a straight-chained or branched alkyl chain with 1–6 carbon atoms, preferably methyl, ethyl, propyl, isopropyl, butyl, isobutyl, t-butyl, pentyl, hexyl, neopentyl, thexyl or phenyl, choline, ethanolamine, carnitine, C$_5$–C$_7$-cycloalkyl residue, benzyl or one of the following groups

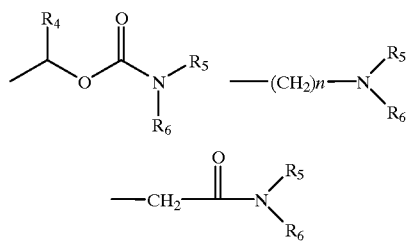

n denotes 0, 1 or 2 and
m represents 0, 1, 2, or 3,
tautomers thereof, their physiologically tolerated salts of inorganic or organic bases as well as processes for the production thereof and pharmaceutical agents containing these compounds.

Since the compounds of the general formula I contain asymmetric carbon atoms all optically active forms and racemic mixtures of these compounds are also a subject matter of the present invention.

Compounds of formula I are also understood to include salts, tautomers, esters, optically active forms and racemic mixtures in the following.

The therapy of malignant neoplasias (carcinomas, sarcomas, haematological neoplasias), inflammatory diseases or autoimmune diseases as well as diseases caused by viruses or retroviruses such as for example AIDS, ARC (AIDS related complex), cytomegaly infections, herpes infections or hepatitis is often also accompanied by the extreme side-effects in addition to the inadequate efficacy of the therapeutic substances used. This effect can be explained by the inadequate in vivo selectivity and limited therapeutic range of the pharmacologically active substances used. The advantageous pharmacological in vitro properties of the pharmacologically active substances can often not be transferred to in vivo conditions.

It has therefore been attempted for years to provide new substances with improved properties with regard to their therapeutic range by modifying the chemical structure of pharmacologically active substances. Moreover new pharmaceutical forms of administration are often developed with the aim of transporting the active substances specifically to their site of action at which they are intended to display their therapeutic action. In this case it is particularly intended to avoid undesired interaction with healthy cells. One possibility to improve the therapeutic range is to change the physical properties of the underlying active substance in such a way that the solubility or tolerance of the active substance is improved by slight modification of the pharmacologically active substance for example by producing acid or base addition salts or by preparing pharmacological safe esters [for example fatty acid esters; J. Pharm. Sci. 79, 531 (1990]. These slightly chemically modified compounds are often denoted "prodrugs" since they are almost immediately converted into the therapeutically active agent on contact with body fluids or in the liver (first pass metabolism). Said 'prodrugs' are included into the invention.

In order to improve catabolic stability, nucleosides such as e.g. ara-C and ara-A have been chemically bound to phospholipids. The corresponding derivatives exhibited less toxicity and higher stability in vivo compared to unmodified nucleosides. The absorption, and cell penetration were, however, hardly influenced. [J. Med. Chem. 32, 367 (1989), Cancer Res. 37, 1640 (1977) and 41, 2707 (1981)]. Further phospholipid derivatives of nucleosides are for example known from the following literature references:

The production and use of liponucleotides as antiviral pharmaceutical agents is described in J. Biol. Chem. 265 6112 (1990). However, in this case only dimyristoylphosphatidyl and dipamitylphosphatidyl residues coupled to the known nucleosides such as AZT and ddC with their fatty acid ester structure were investigated and synthesized.

Nucleoside conjugates of thioether lipids with cytidine diphosphate which have an antitumoral action and could be used in oncology are described in J. Med. Chem. 33, 1380 (1990).

In Chem. Pharm. Bull. 36, 209 (1988) 5'-(3-SN-phosphatidyl)-nucleosides having antileukaemic action are described as well as their enzymatic synthesis from the appropriate nucleosides and phosphocholines in the presence of phospholipase D with transferase activity.

The enzymatic synthesis of liponucleotides is also described inter alia in Tetrahedron Lett. 28, 199 (1987) and Chem. Pharm. Bull. 36 5020 (1988).

WO 94/13324 describes orally available active substances with 1-O-alkyl, 1-O-acyl, 1-S-acyl and 1-S-alkyl-sn-glycero-3-phosphates as lipid carriers.

The application EP 418814 and J. Med. Chem. 34, 1912 (1991) describe isoprenoidphoshydroxyphinylformates as squalene synthetase inhibitors.

In Biochem. Biophys. Res. Commun. 171, 458 (1990) a lipid conjugate of the antiretroviral Foscarnet with palmitylphosphonoformate is described and the anti-HIV activity of (hexyloxy)-hydroxyphosphinylacetic acid is demonstrated in J. Med. Chem. 20, 660 (1977).

In general it is very advantageous to find effective ways of transporting concentrations of therapeutic pharmaceutical substances into the respective target organs or target cells for example in the case of AIDS into the cells of the immune system and the lymphatic system which are considered to be the main reservoir of viral replication.

PFA (phosphonoformic acid) and PAA (phosphonoacetic acid) have good antiviral activity against HSV 1 and 2, influenza, HBV, VZV, EBV as well as retroviral infections.

PFA/PAA and derivatives thereof may under certain circumstances be an effective alternative/supplement to nucleosides since they inhibit a broad spectrum of DNA and RNA polymerases as well as the RT of retroviruses with adequate selectivity.

PFA and PAA themselves are toxic due to their similarity to pyrophosphate by accumulation in bones.

The compounds of the present invention also have valuable pharmacological properties. They are in particular suitable for the therapy and prophylaxis of infections that are caused by DNA viruses such as the herpex simplex virus, the human herpes virus 6, the cytomegaly virus, papova viruses, the varicella zoster virus, the hepatitis viruses or Epstein-Barr virus, the influenza virus or RNA viruses such as Toga viruses or especially retroviruses such as the oncoviruses HTLV-I and II as well as the lentiviruses visna and human immunodeficiency virus HIV-1 and 2.

The compounds of formula I appear to be particularly suitable for treating the clinical manifestations of retroviral HIV infection in humans such as persistent generalized lymphadenopathy (PGL), the advanced stage of the AIDS-related complex (ARC) and the complete clinical picture of AIDS as well as of associated CMV and HSV infections.

The antiviral/antiretroviral action of Foscarnet (phosphonoformic acid trisodium salt/PFA) in HIV patients with CMV retinitis is described in J. Infect. Dis. 172, 225 (1995).

The antiviral action in murine CMV is described in Antiviral Res. 26, 1 (1995)

In addition PFA is utilized in JAMA 273, 1457 (1995) for the treatment of CMV retinitis.

PFA- and PAA-2',3'-dideoxy-3'-thiacytidine conjugates which inhibit HIV-1 replication are shown in J. Med. Chem. 37, 2216 (1994) and acyloxyalkyl esters of Foscarnet are described in J. Pharm. Sci. 83, 1269 (1994).

However, the U.S. application Ser. No. 5,194,654 and the PCT-Application WO 94/13682 are of particular interest. Lipid derivatives of phosphonocarboxylic acids and their use in liposomes with formation of a particularly stable liposomal complex are described therein. Apart from an extremely broad and very speculative claim, 1-O-alkyl-sn-glycero-3-phosphonocarboxylic acids are described as the core of the application which are incorporated particularly well into the lipid bilayer of liposomes. The claimed alkyl residues can comprise 2–24 carbon atoms.

Only the compound 1-O-octadecyl-sn-glycero-3-phosphono-formate(batylphosphonoformate) is described as an example and supported by data for an antiviral action. This compound proved to be unstable in the investigations and during production. In contrast to the said patent applications the compound is used as the pure substance in solution/suspension and not in liposomes.

The compounds of the general formula I according to the invention are stable under the same conditions and have clear advantages in vitro as well as in vivo (MCMV-model in the mouse). Especially the carboxylic acid esters are stable when administered orally and have a better bioavailability than the corresponding free carboxylic acids.

A very close structure-action relationship was surprisingly found with regard to the chain length of the saturated alkyl residues used. Only the use of two alkyl residues in the chain length range of 10–13 carbon atoms shows optimal effects.

The compounds claimed in this application therefore represent an improvement compared to WO 94/13682 and U.S. Pat. No. 5,194,654 which was not to be expected and although they are encompassed by these applications they do not represent the core of the application and are not explicitly mentioned or mentioned by name and neither would their use be made obvious by them.

The compounds of formula I are new. In addition to the improved stability (in substance and in solution) the claimed compounds also have a better action compared to the known lipid derivatives.

Surprisingly the pharmaceutical substances of formula I have a broader therapeutic range compared to the pharmacologically active free and unmodified substances.

Moreover they improve their retention time in the body, the bioavailability or the membrane permeability (e.g. blood-brain barrier, cell membrane etc.) of the pharmacologically active substances which is often known to be a critical factor. Compounds of formula I thus serve as a carrier system (carrier) for the pharmacologically active substances. With regard to their function the conjugates of formula I can be referred to as an intracellular drug storage, drug targeting and drug delivery system. They enable the pharmacologically active substance to be released intracellularly after oral administration and advantageously this release does not take place unspecifically in all cells, organs or tissues of the body but specifically in those cells that contain a particular enzyme. However, it is particularly surprising that cleavage does not already occur during the transport of the substrate by the body fluids such as blood, serum or lymph fluid or by the liver but only on or in the respective target cells. In this way undesired excretion of the phosphonocarboxylic acid by the kidney or cleavage of the conjugate in the liver is avoided so that the major part of the active substance is transported to or into the respective target cells. As already stated above such cells are in particular physiologically or pathophysiologically activated cells which come into consideration as a target object for the administration of pharmacologically active substances such as for example blood leucocytes, lymphocytes, macrophages and other cell populations of the immunological lymphatic system. These are in particular activated cells (e.g. macrophages, granulocytes, lymphocytes, leucocytes, thrombocytes, monocytes etc.) which play a pathophysiological or symptomatic role in the respective disease process. In addition these are cells which are infected by viruses, bacteria, fungi or other microorganisms.

Surprisingly it was also found that the therapeutic range of a pharmacologically active phosphonocarboxylic acid and esters thereof is significantly improved when the substance is coupled to a very special lipid-like carrier molecule. The conjugate prepared in this way serves as a new active substance for the production of pharmaceutical forms of administration. On the whole the coupling results in an increased in vivo effect of the pharmaceutically active phosphonocarboxylic acid since the pharmacologically active substance is localized in the target cells by the resulting drug delivery transport system and hence the efficiency and tolerance of the pharmacologically active substance is improved. This means that on the one hand the amount of the pharmacologically active phosphonocarboxylic acid to be administered can be reduced or on the other hand it is possible to achieve an increased pharmacological effect while retaining the same effective amount.

The pharmacologically active phosphonocarboxylic acid is released from the conjugate by enzymatic hydrolysis of the conjugate.

The conjugates of formula I exhibit significant advantages in comparison with the unconjugated pharmacologically active phosphonocarboxylic acid or its ester. The specific carrier covalently bound to the pharmacologically active substance improves the bioavailability of the poorly resorbed pharmacologically active substances, the tolerance of potentially toxic active molecules, the retention time of rapidly eliminated or metabolized pharmaceutical agents and the membrane penetration of compounds with poor membrane permeability (e.g. blood-brain, cells etc.).

The enzymatic cleavage of the lipid moiety in vivo usually does not occur in the serum but only intracellularly. In addition the carrier moiety with its lecithin-like structure, which is essential for the claimed effect, improves the penetration or membrane permeability of the pharmacologically active substance and exhibits a depot effect. Moreover the gastrointestinal tolerance of the lipid conjugates is considerably better than that of the pure pharmacologically active phosphonocarboxylic acid. The lipid conjugate also exhibits a better penetration through membrane structures during resorption and thus it is more able to overcome the resorption barriers. The same also applies to penetration e.g. the blood-brain barrier.

In addition the in vivo distribution is improved by a better binding of the conjugate to plasma and tissue proteins. The conjugate is primarily oxidized by normal biotransformation from a thioether (n=0) to a sulfoxide (n=1) which, however, due to the equipotent action of the sulfoxide in comparison to the thioether, does not represent a disadvantage. The slow release of the pharmacologically active phosphonocarboxylic acid from the conjugate ensures a low level of active substance that is, however, constant over a long period of time and thus improves the efficacy and/or avoids toxic side effects. The released pharmacologically active substance in the form of a monophosphate no longer penetrates from the cell due to its high hydrophilicity.

The total body, cell as well as the organ half-lives of the pharmacologically active substance are considerably extended by the conjugation due to the longer retention time of the conjugate in the organism. Due to the lack of cleavage activity in serum and in various organs, almost no or only slight bone marrow and organ toxicity can be observed. It is particularly advantageous that the conjugates of formula I are specifically accumulated in various target organs, tissue or cells.

The compounds of formula I can be used as active substances for the production of pharmaceutical agents which can be used for all diseases in which a high level of pharmacologically active substance in cells, organs or tissues is required or is beneficial. An essential requirement for this system denoted "drug-storage-delivery-targeting" is that the cells which are to respond in accordance with the intended therapy have the cleavage enzyme so that the active substance binds in a first step and is subsequently transported through the cell membrane into the interior of the cell in the process of which the active substance is cleaved to form the physiologically active phosphonocarboxylic acid either essentially simultaneously with the transport through the cell membrane or even later partially within the cell. Intracellular cleavage takes place especially in those cases in which the cleavage e☐zyme is also located within the cell.

Suitable target cells are for example cells of the immunological lymphatic system (e.g. blood leucocytes, monocytes, macrophages, lymphocytes) or infected cells.

Surprisingly it was also found that compounds of the general formula I inhibit the multiplication of DNA or RNA viruses at the level of virus-specific DNA or RNA transcription. The substances can influence the reproduction of retroviruses by inhibiting the enzyme reverse transcriptase (cf. Proc. Natl. Acad. Sci. USA 83, 1911, 1986 and Nature 325, 773, 1987). The inhibitory action on the HI virus, the cause of the immune deficiency disease AIDS is of particular therapeutic interest. Nowadays 3'-Azido-3'-deoxythymidine (DE-A-3608606) is approved among others for the treatment of AIDS in AIDS patients. However toxic side effects of 3'-azido-3'-deoxythymidine on the bone marrow necessitate blood transfusions in about 50% of the treated patients. The compounds of the general formula I do not have these disadvantages. They have antiviral efficacy without being cytotoxic in pharmacologically relevant doses.

The compounds of the present invention and their pharmaceutical preparations can also be used in combination with other pharmaceutical agents for the treatment and prophylaxis of the above-mentioned infections. Examples of these agents containing further pharmaceutical agents that can be used for the treatment and prophylaxis of HIV infections or diseases which accompany this disease are 3'-azido-3'-deoxythymidine, 2',3'-dideoxynucleosides such as 2',3'-dideoxycytidine, 2',3'-dideoxyadenosine and 2',3'-dideoxyinosine, acyclic nucleosides (e.g. Acyclovir), non-nucleosidic RT inhibitors, protease inhibitors such as e.g. Invirase, interferons such as interferon $\alpha$, $\beta$, $\gamma$, cytokines and interleukins (e.g. interleukin 16), chemokines such as MIP1$\alpha$, MIP1$\beta$, CC1, renal excretion inhibitors such as probenicid, nucleoside transport inhibitors such as dipyridamol as well as immuno-modulators such as interleukin II or stimulating factors such as granulocyte macrophage colony stimulating factors (GM-CSF), granulocyte colony stimulating factors (G-CSF, neutropoetin), thrombopoetin and thrombopoetin-like factors. The compounds of the present invention and the other pharmaceutical agent can be administered individually or simultaneously and optionally in a single or two separate formulations or at different times in order to achieve a synergistic effect.

Alkali, alkaline-earth and ammonium salts of the carboxyl and phosphonate group come above all into consideration as possible salts of the compounds of the general formula I. Lithium, sodium and potassium salts are preferred as the alkali salts. Magnesium and calcium salts come in particular into consideration as alkaline-earth salts. Ammonium salts are understood according to the invention as salts which contain the ammonium ion that can be substituted up to four times by alkyl residues with 1–4 carbon atoms and/or by aralkyl residues preferably by benzyl residues. In this case the substituents can be the same or different.

Carboxylic acid esters of the phosphonocarboxylic acid lipid derivatives are understood as pharmacologically acceptable esters and these are preferably esters with a benzyl, choline, ethanolamine, carnitine, $C_5$–$C_7$ cycloalkyl residue or with a straight-chained or branched alkyl residue with 1–6 carbon atoms in particular a methyl, ethyl, propyl, butyl, pentyl, hexyl, isopropyl, i-butyl, t-butyl, neopentyl or thexyl residue. Methyl, ethyl, propyl, butyl, t-butyl and benzyl are quite particularly preferred.

The lipid phosphonocarboxylic acid esters are in vitro as effective as the respective free carboxylic acids. However, in vivo they have significant advantages especially when administered orally.

The carboxylic acid esters of the compounds of formula I exhibit a lower decomposition by decarboxylation in an acidic medium and thus they have an improved bioavailability. The dose to be administered can therefore be reduced several times compared to the respective free carboxylic acid. In addition the membrane permeability is improved e.g. when overcoming the blood-brain barrier and when passing through the cell membrane into the target cell. Since the carboxylic acid ester has to be firstly cleaved in vivo by esterases, the half-life in serum is increased.

$R^1$ in the general formula I preferably represents a straight-chained $C_{10}$–$C_{12}$ alkyl group. $R^1$ in particular represents a decyl, undecyl, dodecyl or tridecyl group.

n is preferable one of the numbers 0 or 1.

$R^2$ preferably denotes a straight-chained $C_9$–$C_{12}$ alkyl group.

$R^2$ in particular represents a decyl, undecyl or dodecyl group.

Preferred coupled phosphonic acids and esters thereof in the claimed conjugates of the general formula I are the following acids and their esters:

phosphonoformic acid phosphonoacetic acid phosphonopropionic acid

Especially preferred lipid moieties are n=0 and the combination $R_1$=decyl/$R_2$=dodecyl, $R_1$=undecyl/$R_2$=undecyl or $R_1$=dodecyl/$R_2$=decyl, and in addition $R_1$=undecyl/$R_2$=decyl, $R_1$=tridecyl/$R_2$=decyl, $R_1$=dodecyl/$R_2$=undecyl.

The compounds of the general formula I can be prepared by 1. reacting a compound of the general formula II,

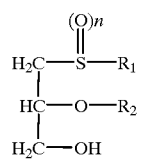

in which $R_1$, $R^2$ and n have the stated meanings with a compound of the general formula III,

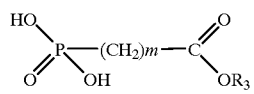

in which m has the meaning given above and $R^3$ represents one of the above-mentioned ester residues, in the presence of an optionally substituted arylsulfonic acid chloride in an organic base or in the presence of the base in an inert organic solvent and optionally the carboxylic acid ester is subsequently converted into a derivative of formula I or a physiologically compatible salt thereof by means of alkaline saponification; or 2. a mixed anhydride is prepared from a compound of formula III and an alkyl- or arylsulfonic acid chloride and is reacted in the presence of a base in an inert organic solvent or directly in the base with an alcohol of formula II and optionally the carboxylic acid ester is subsequently alkaline saponified; or 3. a phosphonocarboxylic acid of formula III in which R denotes hydrogen is reacted with an alcohol of formula II in the presence of a base and an optionally substituted arylsulfonic acid chloride and if necessary it is converted into a physiologically acceptable salt; or 4. a mixed anhydride of a compound of formula III in which R denotes hydrogen and an alkyl- or arylsulfonic acid chloride is reacted in the presence of a base optionally in an inert organic solvent with an alcohol of formula II and the conjugate is optionally converted into a physiologically compatible salt; or 5. Phosphonic acud dichloride of the general formula IV

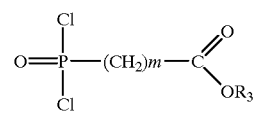

which is synthesized as described in Bhongle et al. (Synthetic Commun. 17, 1071 (1987)) starting from a phosphonic acid bis-trimethylsilyl ester and following reaction with oxalylchloride, reacts afterwards with an alcohol of the general formula II together with a base in molar ratio of 1:1. or 6. a compound of formula III is converted with oxalyl chloride as described in Tetrahedron Letters Vol. 33, No. 49, pp. 7473–7474 into the respective phosphonic acid dichloride of formula IV which is subsequently reacted with an alcohol of formula II in the presence of a base in a molar ratio of 1:1. The phosphonic acid monochloride that forms as an intermediate is saponified to form a semiester and the carboxylic acid ester is converted into a derivative of formula I or a physiologically compatible salt thereof by alkaline saponification.

The free acids of the lipid derivatives of phosphonocarboxylic acids can optionally be converted into the desired esters.

Compounds of formula II and their production are described in EP-0545699 and the examples.

The pharmaceutical agents containing compounds of formula I for the treatment of for example viral infections can be administered enterally or parenterally in a liquid or solid form. In this case the usual forms of administration come into consideration such as for example tablets, capsules, dragees, syrups, solutions or suspensions. Water is preferably used as an injection medium which contains the additives usually used in injection solutions such as stabilizers, solubilizers and buffers. Such additives are for example tartrate and citrate buffer, ethanol, complexing agents such as ethylene-diamine tetraacetic acid and non-toxic salts thereof, high-molecular polymers such as liquid polyethylene oxide to regulate viscosity. Liquid carriers for injection solutions have to be sterile and are preferably filled into ampoules. Solid carriers are for example starch, lactose, mannitol, methyl cellulose, talcum, highly-dispersed silicic acids, higher molecular fatty acids such as stearic acid, gelatin, agar—agar, calcium phosphate, magnesium stearate, animal and vegetable fats, solid high-molecular polymers such as polyethylene glycols etc. Suitable preparations for oral application can optionally contain flavourings and sweeteners.

In principle the compounds of formula I can be administered orally, intratracheally, rectally, nasally, vaginally, lingually, intravenously, intraarterially, intramuscularly, intradermally or subcutaneously. The dose can depend on various factors such as manner of application, species, age or individual state. The compounds according to the invention are usually administered in amounts of 0.1–1000 mg preferably 2–800 mg quite preferable 30–250 mg per day and per kg body weight. It is preferable to divide the daily dose into 2–5 applications, 1–2 tablets with a content of active substance of 0.5–3000 mg being administered at each application. The tablets can also be retarded by which means the number of applications can be decreased to 1–3 per day. The content of active substance of the retarded tablets can be 20–5000 mg. The active substance can also be administered as a continuous infusion, amounts of 5–10000 mg per day being normally adequate.

Apart from the compounds mentioned in the examples and compounds derived by combining all meanings of the substituents stated in the claims the following compounds of formula I also come into consideration within the sense of the present invention:

1. (3-Dodecylmercapto-2-decyloxy)propoxy hydroxy-phosphinyl-formic acid
2. (3-Dodecylsulfinyl-2-decyloxy)propoxy hydroxy-phosphinyl-formic acid
3. (3-Dodecylsulfonyl-2-decyloxy)propoxy hydroxy-phosphinyl-formic acid
4. (3-Undecylmercapto-2-decyloxy)propoxy hydroxy-phosphinyl-formic acid
5. (3-Decylmercapto-2-decyloxy)propoxy hydroxy-phosphinyl-formic acid
6. (3-Tridecylmercapto-2-decyloxy)propoxy hydroxy-phosphinyl-formic acid
7. (3-Undecylmercapto-2-undecyloxy)propoxy hydroxy-phosphinyl-formic acid
8. (3-Undecylsulfinyl-2-undecyloxy)propoxy hydroxy-phosphinyl-formic acid
9. (3-Undecylsulfonyl-2-undecyloxy)propoxy hydroxy-phosphinyl-formic acid
10. (3-Dodecylmercapto-2-undecyloxy)propoxy hydroxy-phosphinyl-formic acid
11. (3-Decylmercapto-2-dodecyloxy)propoxy hydroxy-phosphinyl-formic acid
12. (3-Undecylmercapto-2-dodecyloxy)propoxy hydroxy-phosphinyl-formic acid
13. (3-Dodecylmercapto-2-dodecyloxy)propoxy hydroxy-phosphinyl-formic acid
14. (3-Dodecylmercapto-2-nonyloxy)propoxy hydroxy-phosphinyl-formic acid
15. (3-Undecylmercapto-2-nonyloxy)propoxy hydroxy-phosphinyl-formic acid
16. (3-Dodecylmercapto-2-octyloxy)propoxy hydroxy-phosphinyl-formic acid
17. (3-Dodecylmercapto-2-decyloxy)propoxy hydroxy-phosphinyl-propionic acid
18. (3-Dodecylsulfinyl-2-decyloxy)propoxy hydroxy-phosphinyl-propionic acid
19. (3-Dodecylsulfonyl-2-decyloxy)propoxy hydroxy-phosphinyl-propionic acid
20. (3-Undecylmercapto-2-decyloxy)propoxy hydroxy-phosphinyl-propionic acid
21. (3 -Decylmercapto-2-decyloxy)propoxy hydroxy-phosphinyl-propionic acid
22. (3-Tridecylmercapto-2-decyloxy)propoxy hydroxy-phosphinyl-propionic acid
23. (3-Undecylmercapto-2-undecyloxy)propoxy hydroxy-phosphinyl-propionic acid
24. (3-Undecylsulfinyl-2-undecyloxy)propoxy hydroxy-phosphinyl-propionic acid
25. (3-Undecylsulfonyl-2-undecyloxy)propoxy hydroxy-phosphinyl-propionic acid
26. (3-Dodecylmercapto-2-undecyloxy)propoxy hydroxy-phosphinyl-propionic acid
27. (3-Decylmercapto-2-dodecyloxy)propoxy hydroxy-phosphinyl-propionic acid
28. (3-Undecylmercapto-2-dodecyloxy)propoxy hydroxy-phosphinyl-propionic acid
29. (3-Dodecylmercapto-2-dodecyloxy)propoxy hydroxy-phosphinyl-propionic acid
30. (3-Dodecylmercapto-2-nonyloxy)propoxy hydroxy-phosphinyl-propionic acid
31. (3-Undecylmercapto-2-nonyloxy)propoxy hydroxy-phosphinyl-propionic acid
32. (3-Dodecylmercapto-2-octyloxy)propoxy hydroxy-phosphinyl-propionic acid
33. (3-Dodecylmercapto-2-decyloxy)propoxy hydroxy-phosphinyl-acetic acid
34. (3-Dodecylsulfinyl-2-decyloxy)propoxy hydroxy-phosphinyl-acetic acid
35. (3-Dodecylsulfonyl-2-decyloxy)propoxy hydroxy-phosphinyl-acetic acid
36. (3-Undecylmercapto-2-decyloxy)propoxy hydroxy-phosphinyl-acetic acid
37. (3-Decylmercapto-2-decyloxy)propoxy hydroxy-phosphinyl-acetic acid
38. (3-Tridecylmercapto-2-decyloxy)propoxy hydroxy-phosphinyl-acetic acid
39. (3-Undecylmercapto-2-undecyloxy)propoxy hydroxy-phosphinyl-acetic acid
40. (3-Undecylsulfinyl-2-undecyloxy)propoxy hydroxy-phosphinyl-acetic acid
41. (3-Undecylsulfonyl-2-undecyloxy)propoxy hydroxy-phosphinyl-acetic acid
42. (3-Dodecylmercapto-2-undecyloxy)propoxy hydroxy-phosphinyl-acetic acid
43. (3-Decylmercapto-2-dodecyloxy)propoxy hydroxy-phosphinyl-acetic acid
44. (3-Undecylmercapto-2-dodecyloxy)propoxy hydroxy-phosphinyl-acetic acid
45. (3-Dodecylmercapto-2-dodecyloxy)propoxy hydroxy-phosphinyl-acetic acid
46. (3-Dodecylmercapto-2-nonyloxy)propoxy hydroxy-phosphinyl- acetic acid
47. (3-Undecylmercapto-2-nonyloxy)propoxy hydroxy-phosphinyl-acetic acid
48. (3-Dodecylmercapto-2-octyloxy)propoxy hydroxy-phosphinyl-acetic acid
49. (3-Dodecylmercapto-2-decyloxy)propoxy hydroxy-phosphinyl-formic acid methyl ester
50. (3-Undecylmercapto-2-decyloxy)propoxy hydroxy-phosphinyl-formic acid methyl ester
51. (3-Tridecylmercapto-2-decyloxy)propoxy hydroxy-phosphinyl-formic acid methyl ester
52. (3-Undecylmercapto-2-undecyloxy)propoxy hydroxy-phosphinyl-formic acid methyl ester
53. (3-Dodecylmercapto-2-undecyloxy)propoxy hydroxy-phosphinyl-formic acid methyl ester
54. (3-Decylmercapto-2-dodecyloxy)propoxy hydroxy-phosphinyl-formic acid methyl ester
55. (3-Dodecylmercapto-2-decyloxy)propoxy hydroxy-phosphinyl-acetic acid methyl ester
56. (3-Undecylmercapto-2-decyloxy)propoxy hydroxy-phosphinyl-acetic acid methyl ester
57. (3-Tridecylmercapto-2-decyloxy)propoxy hydroxy-phosphinyl-acetic acid methyl ester
58. (3-Undecylmercapto-2-undecyloxy)propoxy hydroxy-phosphinyl-acetic acid methyl ester
59. (3-Dodecylmercapto-2-undecyloxy)propoxy hydroxy-phosphinyl-acetic acid methyl ester
60. (3-Decylmercapto-2-dodecyloxy)propoxy hydroxy-phosphinyl-acetic acid methyl ester
61. (3-Dodecylmercapto-2-decyloxy)propoxy hydroxy-phosphinyl-formic acid ethyl ester
62. (3-Undecylmercapto-2-decyloxy)propoxy hydroxy-phosphinyl-formic acid ethyl ester
63. (3-Tridecylmercapto-2-decyloxy)propoxy hydroxy-phosphinyl-formic acid ethyl ester
64. (3-Undecylmercapto-2-undecyloxy)propoxy hydroxy-phosphinyl-formic acid ethyl ester 65. (3-Dodecylmercapto-2-undecyloxy)propoxy hydroxyphosphinyl-formic acid ethyl ester
66. (3-Decylmercapto-2-dodecyloxy)propoxy hydroxyphosphinyl-formic acid ethyl ester
67. (3-Dodecylmercapto-2-decyloxy)propoxy hydroxyphosphinyl-acetic acid ethyl ester
68. (3-Undecylmercapto-2-decyloxy)propoxy hydroxyphosphinyl-acetic acid ethyl ester
69. (3-Tridecylmercapto-2-decyloxy)propoxy hydroxyphosphinyl-acetic acid ethyl ester
70. (3-Undecylmercapto-2-undecyloxy)propoxy hydroxyphosphinyl-acetic acid ethyl ester
71. (3-Dodecylmercapto-2-undecyloxy)propoxy hydroxyphosphinyl-acetic acid ethyl ester
72. (3-Decylmercapto-2-dodecyloxy)propoxy hydroxyphosphinyl-acetic acid ethyl ester
73. (3-Dodecylmercapto-2-decyloxy)propoxy hydroxyphosphinyl-formic acid isopropyl ester
74. (3 -Undecylmercapto-2-decyloxy)propoxy hydroxyphosphinyl-formic acid isopropyl ester
75. (3-Tridecylmercapto-2-decyloxy)-propoxy hydroxyphosphinyl-formic acid isopropyl ester
76. (3-Undecylmercapto-2-undecyloxy)propoxy hydroxyphosphinyl-formic acid isopropyl ester
77. (3-Dodecylmercapto-2-undecyloxy)propoxy hydroxyphosphinyl-formic acid isopropyl ester
78. (3-Decylmercapto-2-dodecyloxy)propoxy hydroxyphosphinyl-formic acid isopropyl ester
79. (3-Dodecylmercapto-2-decyloxy)propoxy hydroxyphosphinyl-acetic acid isopropyl ester
80. (3-Undecylmercapto-2-decyloxy)propoxy hydroxyphosphinyl-acetic acid isopropyl ester
81. (3-Tridecylmercapto-2-decyloxy)propoxy hydroxyphosphinyl-acetic acid isopropyl ester
82. (3-Undecylmercapto-2-undecyloxy)propoxy hydroxyphosphinyl-acetic acid isopropyl ester
83. (3-Dodecylmercapto-2-undecyloxy)propoxy hydroxyphosphinyl-acetic acid isopropyl ester
84. (3-Decylmercapto-2-dodecyloxy)propoxy hydroxyphosphinyl-acetic acid isopropyl ester
85. (3-Dodecylmercapto-2-decyloxy)propoxy hydroxyphosphinyl-formic acid neopentyl ester
86. (3-Undecylmercapto-2-decyloxy)propoxy hydroxyphosphinyl-formic acid neopentyl ester
87. (3-Tridecylmercapto-2-decyloxy)propoxy hydroxyphosphinyl-formic acid neopentyl ester
88. (3-Undecylmercapto-2-undecyloxy)propoxy hydroxyphosphinyl-formic acid neopentyl ester
89. (3-Dodecylmercapto-2-undecyloxy)propoxy hydroxyphosphinyl-formic acid neopentyl ester
90. (3-Decylmercapto-2-dodecyloxy)propoxy hydroxyphosphinyl-formic acid neopentyl ester
91. (3-Dodecylmercapto-2-decyloxy)propoxy hydroxyphosphinyl-formic acid neopentyl ester
92. (3-Undecylmercapto-2-decyloxy)propoxy hydroxyphosphinyl-acetic acid neopentyl ester
93. (3-Tridecylmercapto-2-decyloxy)propoxy hydroxyphosphinyl-acetic acid neopentyl ester
94. (3-Undecylmercapto-2-undecyloxy)propoxy hydroxyphosphinyl-acetic acid neopentyl ester
95. (3-Dodecylmercapto-2-undecyloxy)propoxy hydroxyphosphinyl-acetic acid neopentyl ester
96. (3 -Decylmercapto-2-dodecyloxy)propoxy hydroxyphosphinyl-acetic acid neopentyl ester
97. (3-Dodecylmercapto-2-decyloxy)propoxy hydroxyphosphinyl-formic acid benzyl ester
98. (3-Undecylmercapto-2-decyloxy)propoxy hydroxyphosphinyl-formic acid benzyl ester
99. (3-Tridecylmercapto-2-decyloxy)propoxy hydroxyphosphinyl-formic acid benzyl ester
100. (3 Undecylmercapto-2-undecyloxy)propoxy hydroxyphosphinyl-formic acid benzyl ester
101. (3-Dodecylmercapto-2-undecyloxy)propoxy hydroxyphosphinyl-formic acid benzyl ester
102. (3-Decylmercapto-2-dodecyloxy)propoxy hydroxyphosphinyl-formic acid benzyl ester
103. (3-Dodecylmercapto-2-decyloxy)propoxy hydroxyphosphinyl-acetic acid benzyl ester
104. (3-Undecylmercapto-2-decyloxy)propoxy hydroxyphosphinyl-acetic acid benzyl ester
105. (3-Tridecylmercapto-2-decyloxy)propoxy hydroxyphosphinyl-acetic acid benzyl ester
106. (3-Undecylmercapto-2-undecyloxy)propoxy hydroxyphosphinyl-acetic acid benzyl ester
107. (3-Dodecylmercapto-2-undecyloxy)propoxy hydroxyphosphinyl-acetic acid benzyl ester
108. (3-Decylmercapto-2-dodecyloxy)propoxy hydroxyphosphinyl-acetic acid benzyl ester

EXAMPLE 1

R,S-(3-Dodecylmercapto-2-decyloxy)-propoxy-hydroxyphosphinyl-formic acid di-sodium salt (DMDOP-PFA) and the methyl ester DMDOP-PFA-OMe 18.2 ml phosphonoformic acid trimethyl ester is dissolved in 140 ml dichloromethane and admixed with 72.5 ml bromotrimethylsilane while stirring. The mixture is stirred for 2 hours at room temperature, evaporated, the residue is taken up twice in methanol and the solution is again evaporated each time. The residue is taken up in 30 ml absolute pyridine and admixed with a solution of 48.7 g R,S-(3-dodecylmercapto-2-decyloxy)-propan-1-ol. The mixture is evaporated to dryness, the residue is admixed with 47.1 g 2,4,6-tri-isopropyl-benzene sulfochloride and 150 ml absolute pyridine while stirring. The initially viscous suspension gets thinner after ca. 30 min and is stirred for 25 hours at room temperature.

The precipitate is suction filtered and washed with a small amount of pyridine. The filtrate is admixed with 150 ml water while stirring, the mixture is stirred for 30 min at room temperature, evaporated and admixed with ether. The precipitate which again precipitates is removed by filtration and the ether filtrate is shaken out with 0.5 N NCl. The ether phase is washed well with water, dried and evaporated.

The residue (84.2 g) is purified by chromatography on silica gel with dichloromethane/methanol/glacial acetic acid (9:0.5:0.5). The fractions containing R,S-(3-dodecylmercapto-2-decyloxy)propoxy-hydroxyphosphinylformic acid methyl ester (DMDPO-PFA-OMe).

TLC on silica gel:$R_f$=0.3 (acetic acid/acetone/glacial acetic acid/water 10:4:0.5:0.5) $R_f$=0.69 (dichloromethane/methanol 8:2)

In order to saponify the carboxylic acid methyl ester 5 g of the product obtained above is dissolved in 70 ml tetrahydrofuran and admixed with 6.7 ml 2 N NaOH. It is stirred for 4 hours and allowed to stand overnight. The reaction mixture is buffered to pH 8 with 2-ethylhexanoic acid and evaporated. The residue is stirred out with acetone and the precipitated product is suction filtered. 4.1 g of the acid is obtained with an Fp. of 242–246 C (decomposition).

TLC on silica gel:

$R_f$=0.31 (isopropanol/butyl acetate/water/concentrated ammonia 10:6:3:1)

$^{13}$C-NMR in $D_2O$: COOH (d, 175 ppm, $J_{P-C}$=231.4 Hz)

EXAMPLE 2

R,S-(3-dodecylmercapto-2-decyloxy)-propoxy-hydroxyphosphinyl acetic acid di-sodium salt (DMDOP-PAA) and the methyl ester DMDOP-PAA-OMe.

The title compound of Fp. 358–360 C (decomposition) is obtained analogously to example 1 starting with phosphonoacetic acid trimethyl ester as a wax-like product and (3-dodecylmercapto-2-decyloxy)-propan-1-ol.
DMDOP-PAA:
TLC on silica gel:
$R_f$=0. 53 (n-butanol/glacial acetic acid/water 2:1:1)
$R_f$=0.07 (dichloromethane/glacial acetic acid/water 9:0.5:0.5)
DMDOP-PAA-OMe: TLC on silica gel
$R_f$=0.6 (u-butanol/glacial acetic acid/water 2:1:1)
$R_f$=0.1 (dichloromethane/glacial acetic acid/water 9:0.5:0.5)

EXAMPLE 3

Determination of bone marrow toxicity in vitro (CFU-GM assay)

CFU-GM assays were carried out as described by Seidel and Kreja (Seidl, H. and J. Kreja, L., "Blut" 47, 139–145, 1983). Bone marrow cells ($1 \times 10^5$ cells/ml) of Balb/c mice were cultured in Iscove medium which contained 0.8% methyl cellulose, 20% horse serum, $10^{-4}$ M α-thioglycerol and an optimal volume (12.5 or 25 µl) of endotoxin-activated mouse serum which had been obtained from Balb/c mice 4 hours after i.v. injection of 50 µg endotoxin per animal (Salmonella abortus equi; Sigma, Deisenhofen, Germany). After incubating the colonies for 6 days they were stained for a further 24 h with 2-(p-iodophenyl)-3-(p-nitrophenyl)-5-phenyl tetrazolium chloride hydrate (INT, Sigma) and then counted in an automated image processor (Artek 982 B, Biosys GmbH, Karben, Germany).

Table 1 shows the $IC_{50}$ concentrations from several concentration-dependency experiments for phosphonoformic acid, DMDOP-PFA, phosphonoacetic acid, DMDOP-PAA, (3-octadecyloxy-2-hydroxy)-propoxy-hydroxy-phosphinylformic ethyl ester (OOHP-PFAE) and (3-octadecyloxy-2-hydroxy)-propoxy-hydroxy-phosphinylformic acid (OOHP-PFA) compared to the cytostatic agents Cisplatin (Cis-DDP) and Doxorubicin. As can be seen from the table DMDOP-PFA and DMDOP-PAA up to the highest tested concentration of 100 µg/ml show no toxicity on bone marrow stem cells of the granulocytic/monocytic series. While this also applies to phosphonoformic acid, phosphonoacetic acid as well as the conjugates OOHP-PFAE and OOHP-PFA are more toxic than DMDOP-PFA and DMDOP-PAA.

Tab. 1 $IC_{50}$ values (µg/ml) for Cis-DDP, Doxorubicin, phosphonoformic acid (Foscarnet), DMDOP-PFA, phosphonoacetic acid, DMDOP-PAA, OOHP-PFAE and OOHP-PFA in a CFU-GM assay.

| Substance | $IC_{50}$ (µg/ml)[a] |
|---|---|
| Cis-DDP (Cisplatin) | 0.45 ± 0.11 (5) |
| Doxorubicin | 0.046 ± 0.007 (4) |
| phosphonoformic acid (Foscarnet) | >100 (6) |
| DMDOP-PFA | >100 (6) |
| phosphonoacetic acid | 62.88 (2) |
| DMDOP-PAA | >100 (2) |
| OOHP-PFAE | 59.35 (3) |
| OOHP-PFA | 94.49 (3) | a mean value±SEM; n, number of experiments which have been carried out in a concentration-dependent manner in duplicate or triplicate determinations.

EXAMPLE 4

Oral Bioavailability in Murine Cytomegaly Virus (MCMV) Modell

Female Balb/c mice were treated i.p. with a dose of $8 \times 10^5$ PFU (plaque forming units). The survival rate of the animals increased in the order of: untreated<Foscarnet treated<DMDOP-PFA treated<DMDOP-PFA-OMe.

What is claimed is:

1. A compound of the formula I

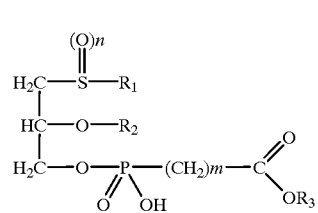

wherein $R_1$ is a straight-chained or branched, saturated or unsaturated $C_9$–$C_{13}$ alkyl chain;

$R_2$ is a straight-chained or branched, saturated or unsaturated $C_8$–$C_{12}$ alkyl chain;

$R_3$ is hydrogen, a straight-chained or branched, saturated or unsaturated $C_1$–$C_6$ alkyl chain, phenyl, choline, ethanolamine, carnitine, $C_5$–$C_7$ cycloalkyl or benzyl, n is 0, 1 or 2 and m is 0, 1, 2 or 3, or a tautomer, optical isomer, racemate, physiologically tolerated ester or physiologically tolerated salt of an inorganic or organic base thereof.

2. The compound of claim 1, wherein $R_1$ is a decyl, undecyl or dodecyl group.

3. The compound of claim 1, wherein $R_2$ is a decyl, undecyl or dodecyl group.

4. The compound of claim 1, wherein n is 0 or 1.

5. The compound of claim 1, wherein m is 0, 1 or 2.

6. The compound of claim 1, wherein $R_3$ is methyl, ethyl, propyl, butyl, t-butyl or benzyl.

7. A pharmaceutical composition comprising a compound according to claim 1 and a pharmaceutically acceptable carrier.

8. A method of treating a condition in a patient in need thereof, wherein the condition is selected from the group consisting of a viral disease and a retroviral disease, the method comprising administering to the patient a condition treating effective amount of a compound according to claim 1.

* * * * *